United States Patent [19]

Favre

[11] Patent Number: 5,246,422

[45] Date of Patent: Sep. 21, 1993

[54] DEVICE FOR CONTINUOUSLY IRRIGATING AND DRAINING HUMAN OR ANIMAL BODY TISSUES OR CAVITIES

[75] Inventor: Pierre Favre, Villars-Mendraz, Switzerland

[73] Assignee: Ferton Holding, Switzerland

[21] Appl. No.: 777,394

[22] PCT Filed: Mar. 28, 1991

[86] PCT No.: PCT/CH91/00081

§ 371 Date: Dec. 2, 1991

§ 102(e) Date: Dec. 2, 1991

[87] PCT Pub. No.: WO91/15149

PCT Pub. Date: Oct. 17, 1991

[30] Foreign Application Priority Data

Apr. 4, 1990 [FR] France .................. 90 04339

[51] Int. Cl.⁵ .................................. A61M 1/00
[52] U.S. Cl. ............................ 604/110; 604/151; 128/DIG. 12
[58] Field of Search ............. 604/151, 153, 110, 27, 604/29, 30, 152; 128/DIG. 12, DIG. 13; 417/477

[56] References Cited

U.S. PATENT DOCUMENTS

| | | | |
|---|---|---|---|
| 3,900,022 | 8/1975 | Widran . | |
| 4,256,437 | 3/1981 | Brown | 604/153 X |
| 4,552,516 | 11/1985 | Stanley | 417/477 |
| 4,722,734 | 2/1988 | Kolln | 604/151 |
| 4,850,972 | 7/1989 | Schulman et al. | 604/110 X |
| 5,041,096 | 8/1991 | Beuchat et al. | 417/477 X |
| 5,125,891 | 6/1992 | Hossain et al. | 604/153 X |

FOREIGN PATENT DOCUMENTS 0293081 11/1988 European Pat. Off. .
86/06964 12/1986 World Int. Prop. O. .

*Primary Examiner*—David Isabella
*Assistant Examiner*—MaryBeth O. Jones
*Attorney, Agent, or Firm*—Davis, Bujold & Streck

[57] ABSTRACT

The device consists of a permanent module (10) and a removable cassette (11). The permanent module comprises a housing (12) with control keys (13) and physical value indicators (14), and two drive hubs (20, 21) for driving two peristaltic pumps mounted in a cassette. The inlet duct (15) of the first pump is connected to a container of physiological liquid, the outlet duct (16) of this pump supplies said liquid to the operating zone, and the duct (17) of the second pump is connected to an operating instrument to drain off the liquid, the duct (18) of this second pump being coupled with a drainage circuit.

10 Claims, 4 Drawing Sheets

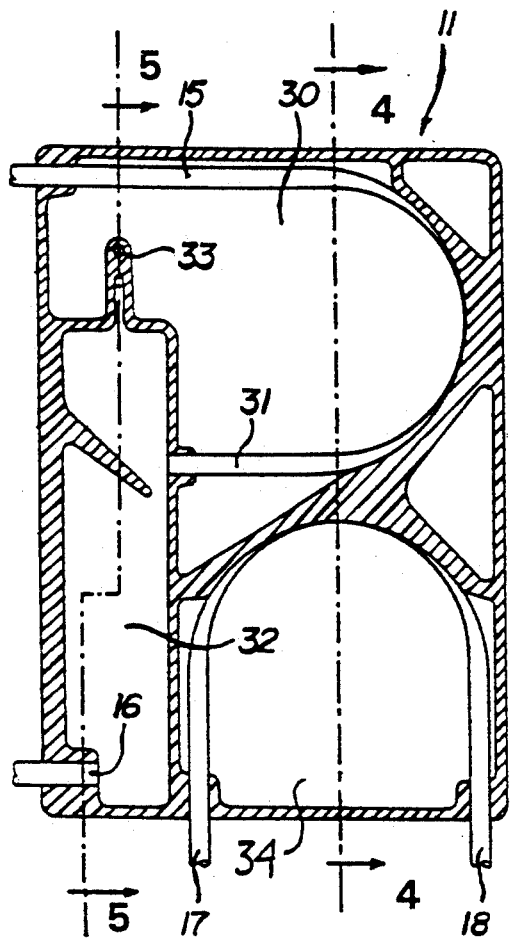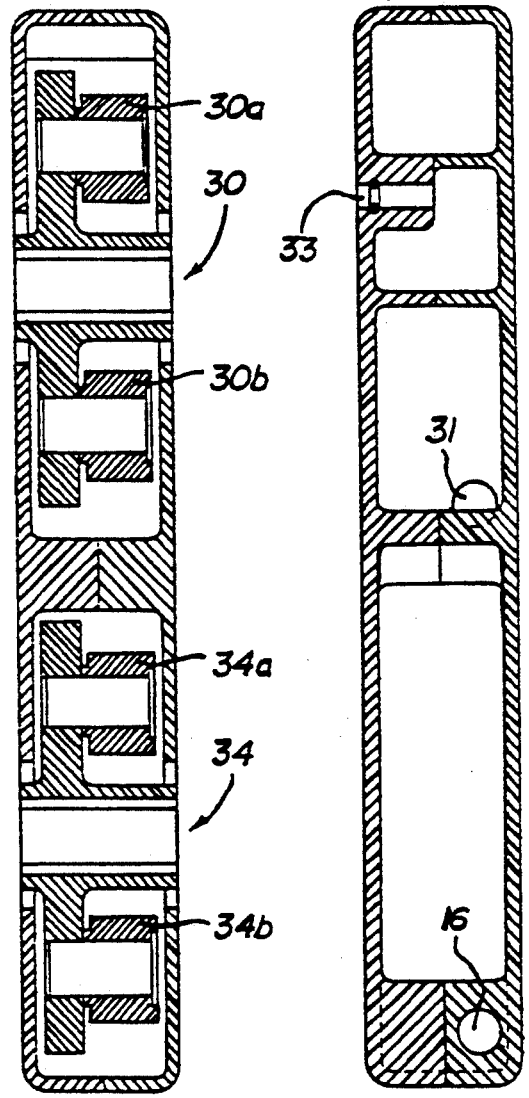
FIG. 3  FIG. 4  FIG. 5

DEVICE FOR CONTINUOUSLY IRRIGATING AND DRAINING HUMAN OR ANIMAL BODY TISSUES OR CAVITIES

The present invention concerns a device for continuous irrigation and drainage of tissues of cavities in the human or animal body with a physiological irrigating liquid during an endoscopic type procedure, said device comprising at least one peristaltic type pump and means for controlling said irrigation.

Endoscopy is a rapidly developing technique in the medical field. It permits a cavity in the human body to be examined using fiberoptic observation techniques. Certain of these cavities must be dilated to permit endoscopic exploration. Presently there are two techniques for such dilation: a technique using gas, such as carbon dioxide, and one using a physiological liquid such as saline or glycine solution. The use of gas is limited to surgery and is gradually disappearing. The first technique is now used only in procedures using transfusions. The second technique, however, which uses injection of a liquid, is becoming more widespread. It is used not only for observation but also for rinsing and evacuating debris. This technique is used in general surgery, in orthopedics, in urology, in gynecology, in otorhinolaryngology, in gastro-intestinal endoscopy, in ophthalmology, etc.

In these different areas, the physiological liquid may circulate in an open or closed circuit. In the case where fluid circulation takes place in a closed circuit, it is necessary to maintain constant pressure in the cavity being explored. In the case where fluid circulation takes place in an open circuit, it is not necessary to maintain constant pressure in the cavity, but rather a generally constant pressure at the outlet of the rinsing nozzle. Open circuit fluid circulation is used in general surgery and otorhinolaryngology, for rinsing gastrointestinal areas and for rinsing open incisions.

At present there are three known ways of obtaining fluid circulation in a closed circuit:
gravity induced flow;
forced flow using a peristaltic pump;
forced flow and aspiration using two peristaltic pumps.

The first technique, based on the principle of gravity induced flow, uses a pouch containing physiological serum, consisting for example of a 0.9% saline solution suspended at a height determined by the surgeon and which is usually of the order of 1 meter above the patient. This pouch is connected to the operating zone by a sterile duct which is itself connected to an instrument such as, for example, an arthroscope introduced into the joint when the procedure is arthroscopy. A drainage duct with a valve is used to drain the liquid, either all at once or continuously, thereby evacuating debris generated during the procedure and continually renewing the supply of serum so the surgeon can follow his/her work visually inside the joint.

The second technique is essentially identical to the preceding one, but the pressure applied in the operating zone is not generated by a column of water, but rather by a peristaltic pump. Draining the liquid takes place by gravity, as before, using a duct with a valve or a control for adjusting flow.

The third technique uses two peristaltic pumps, one placed above the operating zone and one below it. The first one is for conducting liquid to the operating zone and the second is for draining the liquid and the solid or liquid materials it contains. The two pumps are preferably controlled and, at least in theory, ensure constant pressure in the operating zone. When diagnosis or surgery takes place in an open cavity, the methods presently in use derive directly from the gravity distention technique or from the technique of using a peristaltic irrigation pump. Draining the liquid may also be done using an aspiration nozzle connected directly to a vacuum pump provided in the operating area.

At present each type of procedure requires a specific apparatus. Thus, pumps made by the U.S. company 3M or pumps made by the Swiss company ORTHOCONCEPT are used in arthroscopic procedures, irrigation systems sold by the DAVOL company are used for irrigating open incisions, and a pump proposed by the ORTHOCONCEPT company is used for prostate resections.

The fact that such a panoply of specific systems for each procedure must be maintained in the operating room represents a heavy expense which a hospital cannot always bear. Added to the problem of cost are storage problems and difficulties connected with sterilization, which cause confusion and wasted time.

The present invention proposes overcoming the various disadvantages outlined above by placing at the surgeon's disposal a universal apparatus, adaptable to whatever procedure is taking place.

To achieve this, the device according to the invention is characterized in that it comprises a permanent module equipped with at least one motor for driving the pump, with a control circuit for the motor and with means for connecting the motor with the pump, and at least one removable single-use cassette with at least one inlet duct connected to a supply of physiological irrigation liquid, at least one outlet duct to evacuate the liquid from the operating zone, preprogrammed means for providing specific information relating to the type of procedure to the circuit controlling the motor, and preprogrammed means for providing specific information relating to the procedure accomplished to the circuit controlling the motor.

According to a preferred embodiment, the cassette has a coding device designed to identify a predetermined code with the corresponding procedure taking place, while the permanent module contains a means for identifying this code.

In this preferred embodiment, the cassette has a memory device designed to store a predetermined program for controlling the pump in the permanent module according to the procedure which is to take place.

In certain applications the device may have two peristaltic pumps designed for irrigation and drainage of the operating zone, respectively.

According to a first variation, the two pumps are contained in a permanent module.

According to a second variation, the two pumps are contained in a cassette, the drive spindles for these pumps being attached to the permanent module.

In this case, the cassette is provided with at least four ducts corresponding in pairs to each of said peristaltic pumps, a first pair of ducts, one of which is connected to a supply of physiological liquid and the other of which is connected to an operating instrument on the patient to conduct the physiological liquid to the operating zone, and a second pair of ducts, one of which is also connected to a surgical instrument to drain the physiological liquid from the operating zone and the other of which is joined to a drainage circuit.

The cassette may have specific coding means for each type of intervention, and the permanent module may have means for identifying this code.

Preferably, the code means comprise at least one coding device positioned according to the procedure planned and identification means comprising a series of detectors, at least one of which is activated by the coding device on the cassette.

This coding device may be a protruding element located on one surface of the cassette.

The detectors are advantageously mechanically activated switches, optical detectors, magnetic detectors or capacitive detectors.

According to one advantageous embodiment, the device has security means to prevent reuse of the single-use cassette.

These security means may comprise a protruding element integral with the cassette designed to engage in a groove in the permanent module and to break when the cassette is removed.

These security means are advantageously associated with the identification means.

The present invention will be better understood with reference to the description of some exemplary embodiments and to the attached drawing, wherein:

FIG. 3 is a longitudinal cross-section of one cassette of the device according to the invention;

FIG. 4 is a cross-section of the cassette taken along line 4—4 of FIG. 3;

FIG. 5 is a cross-section taken along line 5—5 of the cassette shown in FIG. 3.

Figure 1:
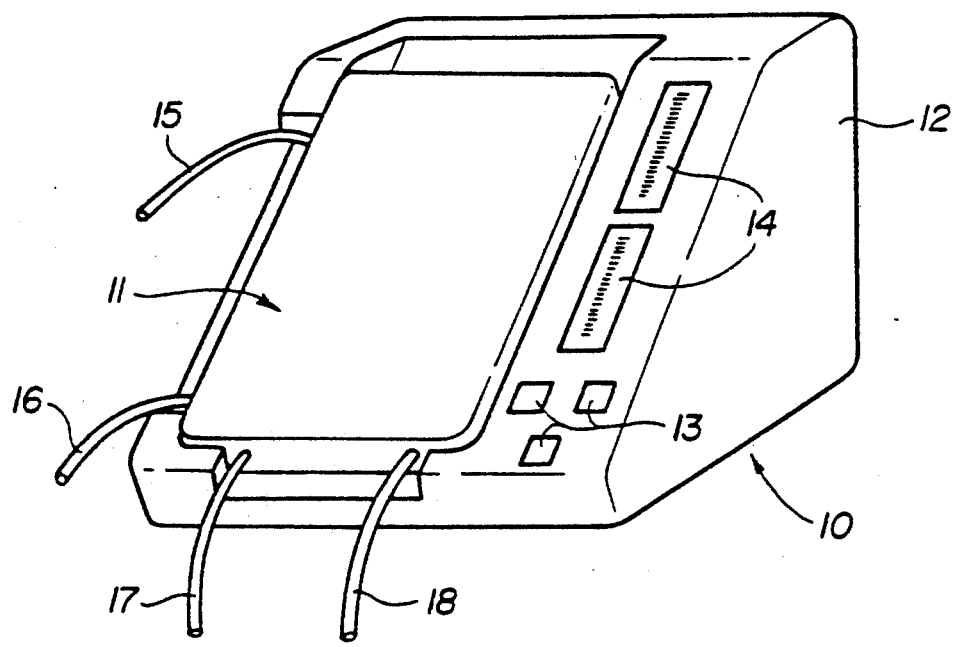
FIG. 1 is a perspective view of an advantageous embodiment of the apparatus according to the invention.

FIG. 1 shows an advantageous embodiment of the device described above which is essentially composed of a permanent module 10 and a removable cassette 11. The permanent module comprises a housing 12 with function keys 13, perhaps on the front surface, and indicators or display devices 14 showing physical conditions such as pressure, flow rate, etc. In the example shown, cassette 11 has a duct 15 supplying physiological liquid, which is designed for connection to a reservoir holding this liquid (not shown), an inlet duct 16 conducting the liquid to the operating zone on the patient, a suction duct 17 designed to suction said physiological liquid from this zone and a drainage duct 18 terminating in a drainage circuit into which the liquid and any debris suctioned from the operating zone flow.

As indicated previously, the cassette corresponds to a given application and on one side, has two peristaltic pumps 50 and 51 respectively corresponding to ducts 15 and 16 and to ducts 17 and 18, and on the other side, means for storing the pump functions and particularly the parameters of pressure, flow rate or other physical parameters which must be controlled for a predetermined patient procedure.

Figure 2:
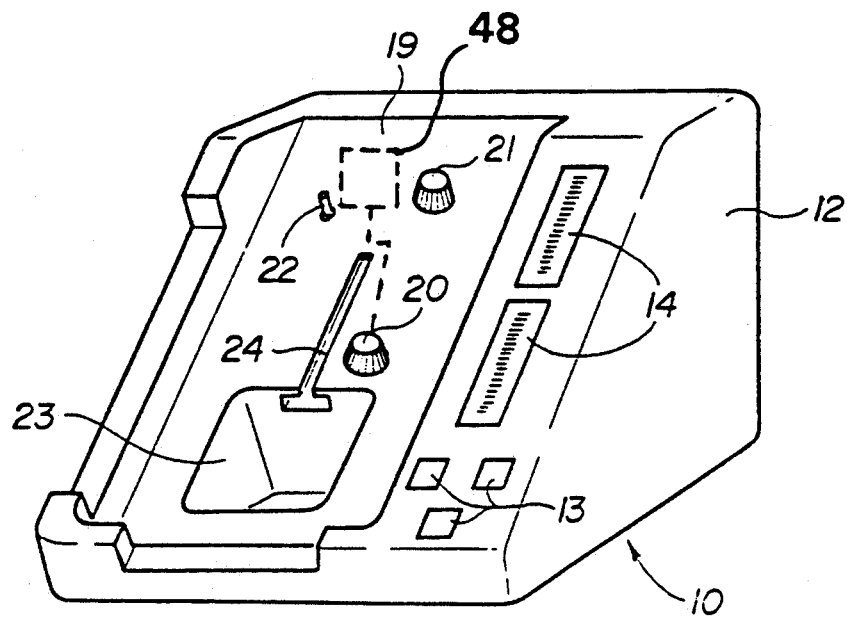
FIG. 2 is a perspective view of the permanent module of the device of FIG. 1.

FIG. 2 is a view of the permanent module with the cassette removed. This permanent module has an opening 19 for engaging a cassette and in which there are two drive spindles 20 and 21, respectively, for the peristaltic pumps 50, 51 housed in cassette 11 (see FIG. 1). At the base of this opening there are also a connecting tip 22 designed for reading pressure, as well as a recessed area 23 and a groove 24 communicating with the cavity, the role of which will be defined later.

In the most up-to-date embodiments, the pumps would be housed in the cassette. However, for certain applications or in certain embodiments, the pumps could be permanently attached in the permanent module.

FIGS. 3, 4 and 5 show a particularly advantageous embodiment of a cassette 11 in more detail. A first peristaltic pump 30, 30a, 30b, shown schematically, is associated with ducts 15 and 16, whose role has been defined above. In the embodiment shown, the exit conduit of peristaltic pump 30 is not duct 16, but a conduit 31 opening into a reservoir 32 which constitutes a reserve of pressure. A pressure detecting connector 33 which communicates with this reservoir measures the pressure of the liquid at the time it is transmitted to the operating zone.

A second peristaltic pump 34, 34a, 34b is associated with the two ducts 17 and 18 whose role has already been defined.

All these elements are contained within a housing, preferably of a suitable molded synthetic material, which constitutes the cassette itself.

FIG. 4 is a cross-section taken along lines 4—4 passing through the axes of the two peristaltic pumps 30 and 34. This drawing shows the rollers 30a and 30b on pump 30 and the rollers 34a and 34b on pump 34.

FIG. 5 shows a cross-section of the cassette taken along line 5—5 and particularly the pressure detecting connector 33, the mouth of conduit 31 and the connection tip of duct 16.

Figure 6:
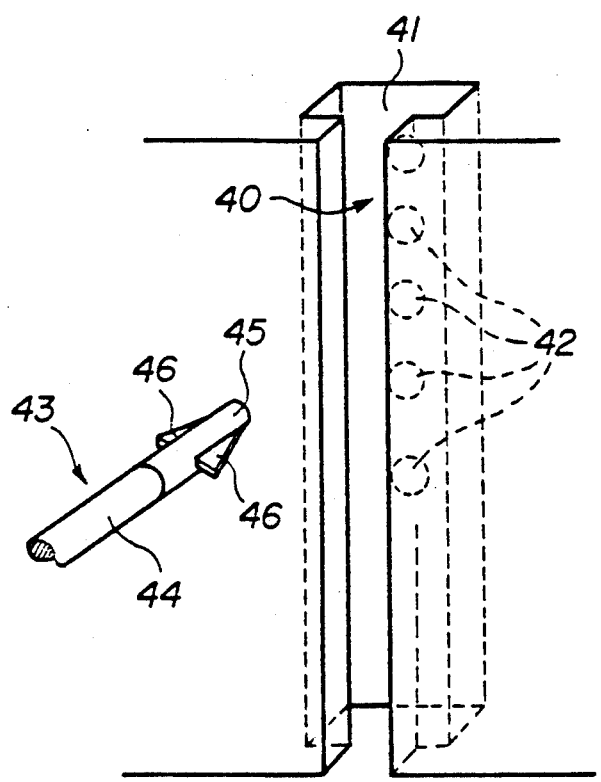
FIGS. 6 and 7 is a detailed view showing the locking system on the device.

FIG. 6 shows a detailed view of groove 24 which is a program selection groove associated with security devices preventing reuse of the cassette. Groove 24 has a particular shape and consists of a narrow passageway 40 connected to an enlarged passageway 41. Along this passageway there are several contacts 42 which select the program for using the device as a function of the procedure to take place. The cassette has a stem 43 which engages in groove 40 in a position corresponding to one of the contacts 42. Because of this, stem 43 is in a first position when the cassette is to be used for a urological procedure, in a second position for a gynecological procedure, in a third position for an arthroscopy, etc. The stem 43 consists of a protruding element 44 extending into a tip 45 with two retractable lateral flanges 46 which can penetrate lateral passageway 41 through narrow passageway 40, but cannot be withdrawn from them. Therefore, when the cassette is removed at the end of the procedure, tip 45 breaks off protruding element 44 and falls into recessed area 23 (see FIG. 2). This device constitutes the safeguard which prevents reuse of the cassette.

Figure 7:
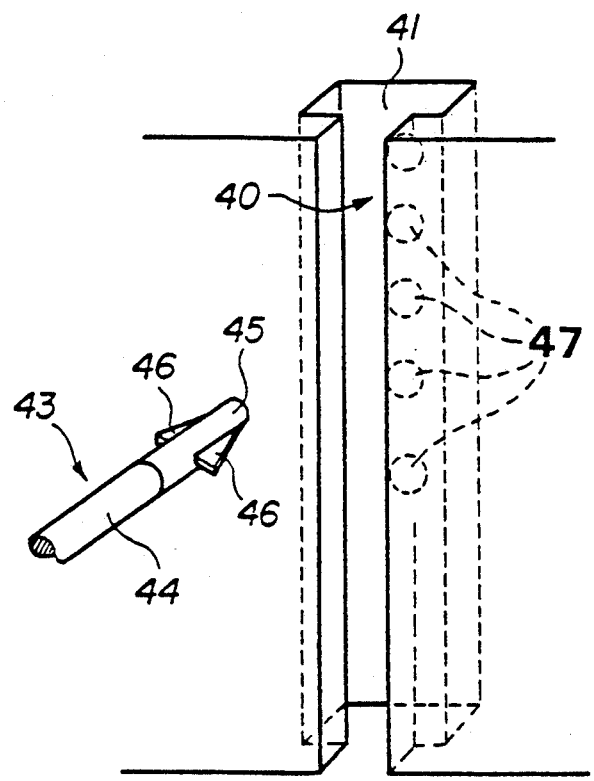

It is apparent that contacts 42 for selecting programs as a function of procedures could be replaced by any other identification detectors such as optical, magnetic, capacitive detectors, etc. shown diagrammatically by generic reference numeral 47 in FIG. 7.

In the case of knee arthroscopy, considerable pressure can be generated by certain knee movements. The device described above is equipped with an electronic control allowing the surgeon to work in complete safety, that is, within a range of pressure maintained within acceptable limits for the procedures in question. Ill-timed pressure increases caused by sudden knee movements theoretically act on the high pressure safeguards by activating the peristaltic pumps. The permanent module has a device which limits pressure increases, thereby preventing the pumps from starting up suddenly. Pressure is regulated with appropriate controls on the peristaltic pumps during procedures.

The device described above may undergo various modifications and assume various embodiments obvious to one skilled in the art. In particular, it is possible to provide only one peristaltic pump on certain cassettes when the corresponding procedure does not require suctioning off physiological liquid and debris from the operating zone. In addition, the shape of the permanent module as well as of the cassettes could be modified. Finally, the functions of the different components could also be modified to take into account specific requirements for each type of procedure made possible by the device.

I claim:

1. A device for irrigation and continuous drainage of tissues or cavities, comprising:
    a) a first peristaltic pump located within a removable disposable cassette, said first peristaltic pump being connected to a first duct means for supplying a physiological liquid for irrigation during an endoscopic type procedure;
    b) a permanent module which mounts the removable disposable cassette, said module including a controllable motor driven first spindle which drivably engages said first peristaltic pump;
    c) program setting means mounted on said removable disposable cassette; and
    d) multiple identifying means mounted on said permanent module, at least one of said multiple identifying means being actuated by said program setting means to effectuate a pump operation regimen of the device associated with a desired one of a plurality of endoscopic procedures.

2. A device according to claim 1, wherein a second peristaltic pump is mounted within said removable disposable cassette, said second peristaltic pump being connected to a second duct means for draining a physiological liquid and drivably engaged by a controllable motor driven second spindle included in said permanent module.

3. A device according to claim 1, wherein said program setting means comprises at least one program setting device at a predetermined location on said removable disposable cassette, said predetermined location corresponding to a predetermined type of endoscopic procedure, said multiple identifying means comprising a series of detectors at least one of which is positioned to be activated by said program selecting device at its predetermined location.

4. A device according to claim 3, wherein said program selecting device comprises a protruding element located on a surface of said removable disposable cassette.

5. A device according to claim 4, wherein said protruding element engages a groove in said permanent module so as to break when said removable disposable cassette is removed from said permanent module thereby to prevent reuse of the cassette.

6. A device according to claim 2, wherein the cassette is equipped with at least four ducts corresponding in pairs to each of said duct means, a first pair of ducts, one of which is for connection to a supply of physiological liquid and the other of which is for connection to an operating instrument on a patient to conduct said physiological liquid to an operating zone, and a second pair of ducts, one of which is for connection an operating instrument to drain physiological liquid from the operating zone and the other of which is for connection to a drainage circuit.

7. A device according to claim 3, wherein the detectors are mechanically activated switches.

8. A device according to claim 3, wherein the detectors are optical detectors.

9. A device according to claim 3, wherein the detectors are magnetic detectors.

10. A device according to claim 3, wherein the detectors are capacitive detectors.

* * * * *